ABSTRACT

United States Patent [19]

Buysch et al.

[11] Patent Number: 5,072,017

[45] Date of Patent: Dec. 10, 1991

[54] PROCESS FOR THE PREPARATION OF P-SUBSTITUTED O-BENZYLPHENOLS

[75] Inventors: Hans-Josef Buysch; Günter Klug, both of Krefeld; Peter Mues, Duisburg; Lothar Puppe, Burscheid, all of Fed. Rep. of Germany

[73] Assignee: Bayer Aktiengesellschaft, Leverkusen, Fed. Rep. of Germany

[21] Appl. No.: 505,799

[22] Filed: Apr. 6, 1990

Related U.S. Application Data

[63] Continuation of Ser. No. 143,544, Jan. 13, 1988, abandoned.

[30] Foreign Application Priority Data

Jan. 14, 1987 [DE] Fed. Rep. of Germany ....... 3700917

[51] Int. Cl.$^5$ ............................................. C07C 255/50
[52] U.S. Cl. ...................................... 558/376; 568/58; 568/628; 568/744; 568/745
[58] Field of Search .................. 558/376; 568/58, 628, 568/744, 745

[56] References Cited

U.S. PATENT DOCUMENTS 4,514,577  4/1985  Filbery et al. ...................... 568/716

FOREIGN PATENT DOCUMENTS 6407636  7/1966  Netherlands .

*Primary Examiner*—Mary C. Lee
*Assistant Examiner*—Jacqueline Haley
*Attorney, Agent, or Firm*—Sprung, Horn, Kramer & Woods

[57] ABSTRACT

Para-substituted o-benzylphenols are prepared by reacting p-substituted phenols with benzylating agents in the presence of zeolites of the faujasite type at elevated temperature.

10 Claims, No Drawings

PROCESS FOR THE PREPARATION OF P-SUBSTITUTED O-BENZYLPHENOLS

This is a continuation of application Ser. No. 07/143,544, filed Jan. 13, 1988, now abandoned.

The invention relates to a process for the preparation of p-substituted o-benzylphenols by reacting p-substituted phenols with benzylating agents in the presence of condensing agents at elevated temperature.

It is known that mixtures of 2-benzylphenols, 4-benzylphenols and 2,6-dibenzylphenols in various ratios are always obtained on benzylation of phenols. Thus, it is known, for example, from J. Amer. Chem. Soc. 53, 2379 (1931) that, on condensation of p-cresol with benzyl alcohol in the presence of aluminium chloride as catalyst, a product mixture is produced which contains 30 to 36% by weight of dibenzylated products, depending on the amount ratio of the starting materials.

It is furthermore known (Abdurasuleva et al., Zh. Org. Khim. 9, 132 (1973)) that up to 18 mole % of dibenzylchlorophenols are produced on benzylation of 4-chlorophenols using benzyl chloride and condensation catalysts, such as $FeCl_3$, $FeSO_4$ or $ZnSO_4$. In addition, Czechoslovakian Patent Specification 170,972 (Chemical Abstracts 89 (1978), 6109 b) describes the condensation of 4-chlorophenol with benzyl chloride in the molar ratio 4:1 in the presence of a sulphonated styrene/divinylbenzene copolymer (=strongly acidic cation exchanger) to form 2-benzyl-4-chlorophenol. Although the yield of the desired product is 83%, relative to reacted 4-chlorophenol, a relatively large amount of higher-boiling products is produced; the ratio of 2-benzyl-4-chlorophenol formed to the higher-boiling products is 4.16:1.

It is disadvantageous in the known processes for the preparation of p-substituted o-benzylphenols that large amounts of dibenzylated products and/or high-boiling byproducts are produced in them and consequently the yields of the desired p-substituted o-benzylphenols are low. The known processes are therefore hardly suitable for industrial preparation of p-substituted o-benzylphenols.

It has now been found that the desired monobenzylation of p-substituted phenols can be achieved without formation of undesired byproducts when the p-substituted phenols are reacted with conventional benzylating agents in the presence of zeolites of the faujasite type.

The invention therefore relates to a process for the preparation of p-substituted o-benzylphenols by reacting p-substituted phenols with conventional benzylating agents in the presence of condensing agents, which process is characterized in that the condensing agents used are zeolites of the faujasite type.

The p-substituted o-benzylphenols obtainable by the process according to the invention can be described by the formula

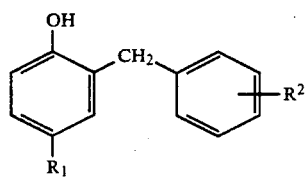

(I)

in which $R^1$ denotes halogen, $C_1$-$C_{12}$-alkyl, $C_1$-$C_{12}$-alkoxy or $C_1$-$C_{12}$-alkylmercapto, and $R^2$ represents hydrogen, halogen, the cyano group, $C_1$-$C_4$-alkyl or a carb-$C_1$-$C_4$-alkoxy group.

The p-substituted phenols to be used as starting compounds in the process according to the invention correspond to the formula

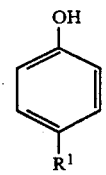

(II)

in which $R^1$ has the meaning mentioned under formula (I). The benzylating agents correspond to the formula

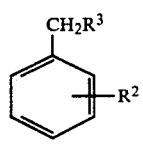

(III)

in which $R^2$ has the meaning given under formula (I) and $R^3$ represents halogen, or a hydroxyl, $C_1$-$C_4$-alkoxy, aralkoxy or aryloxy group.

Suitable alkyl radicals for $R^1$ and in the alkoxy and alkylmercapto groups mentioned for $R^1$ are those having 1 to 12, preferably 1 to 4, carbon atoms. Examples which may be mentioned are: methyl, ethyl, n-propyl, iso-propyl, n-butyl, iso-butyl, sec.-butyl, tert.-butyl, pentyl, hexyl, octyl, decyl and dodecyl, preferably methyl, ethyl, n-propyl, iso-propyl, n-butyl, iso-butyl, sec.-butyl and tert.-butyl, particularly preferably methyl.

Halogens which may be mentioned are: fluorine, chlorine, bromine and iodine, preferably chlorine and bromine, particularly preferably chlorine.

Examples of carb-$C_1$-$C_4$-alkoxy groups which may be mentioned are: the carbomethoxy, the carbethoxy, carbopropoxy and carbobutoxy groups, preferably the carbomethoxy and carbethoxy group.

Aralkoxy groups which may be mentioned are those which contain 1 to 4 C atoms in the alkyl part and 6 to 12 C atoms in the aryl part, for example the 2-phenylethoxy and, particularly, the benzyloxy group.

Aryloxy radicals which may preferably be mentioned are optionally substituted phenoxy radicals; for example the phenoxy, tolyloxy and 4-chlorophenoxy radical.

The following p-substituted phenols, for example, can be employed in the process according to the invention: p-chlorophenol, p-cresol, hydroquinone monoethyl ether, p-hydroxythiophenol, p-bromophenol and p-fluorophenol, preferably p-chlorophenol, p-cresol and hydroquinone monomethyl ether, particularly preferably p-chlorophenol and p-cresol.

Benzylating agents of the formula (II) which may be mentioned as examples are: benzyl chloride, benzyl alcohol, dibenzyl ether and p-chlorophenyl benzyl ether, preferably benzyl alcohol, dibenzyl ether and p-chlorophenyl benzyl ether.

According to the invention, the phenols and the benzylating agents are generally employed in a molar ratio of about 10:1 to 0.1:1 (phenol:benzylating agent), preferably 6:1 to 0.2:1, particularly preferably 5.1:1 to 1.0:1.

The faujasite-type zeolites to be used according to the invention as condensing agents are known and described, for example, by D. W. Breck in Zeolite Molecular Sieves, John Wiley and Sons, Inc. New York 1974, and by Peter A. Jacobs in Carbonionogenic Activity of Zeolites, Elsevier, Amsterdam 1977. Faujasite-type zeolites include both naturally occurring faujasites and synthetic faujasites. In the process according to the invention, synthetic zeolites of the faujasite type are preferably employed; the synthetic faujasite-type zeolites, zeolite X and zeolite Y, are particularly preferred.

Synthetic zeolites of the faujasite type have the general composition:

$(1.0 \pm 0.2)M_{2/n}O \cdot Al_2O_3(2-6)SiO_2 \cdot Z H_2O,$ where
M denotes a metallion and
n its valency.

Zeolite X is the name for synthetic faujasites having a $SiO_2/Al_2O_3$ ratio of 2 to 3, and zeolite Y is the name for synthetic faujasites having a $SiO_2/Al_2O_3$ ratio of 3 to 6.

In the process according to the invention, synthetic faujasites of the X and Y type can be employed in which M denotes a metal cation of groups Ia, IIa, IIIa, IVa, Va, VIa, VIIa, VIIIa, Ib, IIb, IIIb or IVb of the periodic table of the elements (Mendeleyev) or a proton, preferably a metal cation of groups Ia, IIa, IVa or IVb or also a proton, and particularly preferably those in which M denotes a sodium, potassium, caesium, calcium, tin or titanium ion or hydrogen, and very particularly preferred synthetic faujasites are those in which M represents sodium, potassium, caesium, calcium, tin or hydrogen.

The amount of faujasite-type zeolites employed according to the invention is generally about 1 to 50% by weight, preferably 5 to 40% by weight, relative to the phenol employed.

The reaction is normally carried out in the temperature range from about 100° to 250° C., preferably at 125° to 220° C., particularly preferably at 150° to 200° C.

The process according to the invention is generally carried out at atmospheric pressure. However, it can also be carried out at increased or reduced pressure, for example at a pressure from 0.1 to 30 bar, preferably 1 to 10 bar, particularly preferably 1 to 5 bar.

In general, the reaction time for the process according to the invention is about 10 minutes to 50 hours, preferably 30 minutes to 30 hours. However, the reaction time depends essentially on the activity and amount of the zeolite employed.

The reaction according to the invention can be carried out both continuously and batchwise.

When the reaction is complete, the reaction mixture can be worked up in a conventional fashion by vacuum distillation, if appropriate after removing the condensing agent.

The mixture obtained during this distillation in the initial fraction, comprising phenols, benzylating agents and small amounts of the desired product, can be reemployed in the reaction after adding phenols and new benzylating agent.

The o-benzylphenols are obtained in high purity and in yields of more than 90% of theory, relative to reacted phenol, by the process according to the invention.

The process according to the invention can be carried out, for example, as follows:

Molten phenol, the condensing agent and the benzylating agent are introduced into an apparatus, provided with stirrer and reflux condenser, and the reaction mixture is then brought to the suitable reaction temperature. However, it is also possible to add the benzylating agent to the mixture of phenol and zeolite after the reaction temperature has been reached. The reaction is kept at the reaction temperature specified until the benzylating agent has reacted as completely as possible. After removal of the catalyst by filtration, the reaction mixture is distilled in vacuo, the p-substituted o-benzylphenols being obtained in high purity. It is furthermore possible to carry out the vacuum distillation directly after completion of the reaction, i.e. without prior removal of the catalyst. In the continuous procedure, the reaction is expediently carried out in a fixed-bed reactor. In this case, the feed rate (LHSV=amount of starting mixture/amount of catalyst x h) is 0.5 to 5 $h^{-1}$, relative to the mixture of phenol and benzylating agent which is fed at a constant rate in a stream of inert gas (nitrogen, noble gas and/or steam) to the catalyst bed via a preheating section. The reaction mixture emerging from the reactor is fed to a distillation column after condensation.

The advantages of the process according to the invention compared to the prior art are the high yields of p-substituted o-benzylphenols, the high conversion of phenols and the low proportion of high-boiling byproducts, such as dibenzylphenols and other multinuclear aromatics.

p-Substituted o-benzylphenols are known compounds and are employed, according to GB Patent Specification 1,330,753 and U.S. Pat. No. 4,514,577, as antioxidants and bactericides.

The examples below are intended to illustrate the process according to the invention.

EXAMPLES

EXAMPLE 1

68.2 g (0.5 mol) of 4-chlorophenol were reacted with 10.8 g (0.1 mol) of benzyl alcohol for 3 hours at 200° C. in the presence of 6.0 g of Na-Y zeolite. After the catalyst had been removed, 76.2 g of crude product were obtained whose composition was determined by gas chromatography: 71.2% of 4-chlorophenol, 25.4% of 2-benzyl-4-chlorophenol, 0.3% of o-benzylphenol 1.3% of dibenzyl ether and 1.8% of higher-boiling products (including 2,6-dibenzyl-4-chlorophenol). The crude product was distilled in vacuo in a conventional fashion. The initial fraction contained 54.7 g of unreacted chlorophenol containing small proportions of 2-benzyl-4-chlorophenol (<1%). The main fraction from the distillation contained 20.8 g of 2-benzyl-4-chlorophenol (yield 94.8%, relative to 4-chlorophenol employed) and the remainder comprised a higher-boiling oil.

The abbreviations shown below are used below:

| | |
|---|---|
| Z | zeolite |
| CP | 4-chlorophenol |
| BCP | 2-benzyl-4-chlorophenol |
| HB | higher-boiling products = 2.6-dibenzyl-4-chloro- or -4-methyl-phenol and multinuclear aromatics |
| BA | benzyl alcohol |
| BP | o-benzylphenol |
| DBE | dibenzyl ether |
| CPBE | 4-chlorophenyl benzyl ether |

| | |
|---|---|
| PC | p-cresol |
| BPC | 2-benzyl-p-cresol | remainder sum of DBE, CPBE, BA, PCBE and o-benzylphenol.

EXAMPLES 2-7

Table 1 gives the compositions, determined by gas chromatography, of the reaction mixtures of CP and BA as a function of the zeolites used. The CP:BA molar ratios were 1:1. To this purpose, 6.5 g of CP and 5.4 g of BA were heated for 3 hours at 200° C. with 3.0 g of Z.

TABLE 1

| Example | Z | CP | BCP | HB | Remainder | BCP/HB |
|---|---|---|---|---|---|---|
| 2 | H—Y | 23.9 | 52.8 | 15.0 | 8.3 | 3.52 |
| 3 | Na—Y | 17.7 | 63.1 | 15.3 | 3.9 | 4.12 |
| 4 | K—Y | 16.4 | 60.0 | 16.8 | 6.8 | 3.57 |
| 5 | Cs—Y | 27.4 | 51.9 | 15.2 | 5.5 | 3.41 |
| 6 | Na—X | 10.4 | 64.5 | 21.1 | 4.0 | 3.06 |
| 7 | Ca—Y | 32.7 | 39.3 | 10.8 | 17.2 | 3.64 |

The above table shows the high selectivity with which the reaction proceeds when faujasite-type zeolites are employed.

Thus, the formation of higher-molecular-weight byproducts is substantially suppressed, even at such an unfavourable CP:BA molar ratio as 1:1, which is particularly economical since these byproducts must generally be disposed of. In addition, it is clear that Y zeolites and, in this case, particularly Na-Y zeolite give the best results for the present reaction with respect to conversion and suppression of higher-boiling products.

EXAMPLES 8-12

CP and BA were condensed to various molar ratios for 3 hours at 200° C. on Na-Y zeolite. Table 3 shows the composition, determined by gas chromatography, of the reaction mixture.

TABLE 2

| Example | CP:BA | CP | BCP | HB | Remainder | BCP/HB |
|---|---|---|---|---|---|---|
| 8 | 5:1 | 69.7 | 26.5 | 1.8 | 2.0 | 14.8 |
| 9 | 4:1 | 60.1 | 33.7 | 3.4 | 2.8 | 9.9 |
| 10 | 3:1 | 50.1 | 42.5 | 5.0 | 2.4 | 8.5 |
| 11 | 2:1 | 40.3 | 50.4 | 6.8 | 2.5 | 7.4 |
| 12 | 1:1 | 14.5 | 62.6 | 16.5 | 3.9 | 3.8 |

In the abovementioned reaction 1.5 g of Na-Y zeolite were employed. The amount of CP and BA totalled 150 mmol.

Excess CP reduces the formation of high-boiling products since multiple condensations of benzyl alcohol with BCP which has already formed can in this way be avoided to a large extent. Thus, the BCP/HB ratio of 4.16 described in Czechoslovakian Patent Specification 170,972 is exceeded two-fold at a CP:BA molar ratio of 4:1, and even at a CP/BA molar ratio of 2, a BCP/HB ratio of 7.4 is obtained in the process according to the invention.

EXAMPLES 13-15

6.5 g of CP and 5.4 g of BA were brought to the temperature specified in Table 4, and 3.0 g of Na-Y zeolite were then added to the mixture. Table 3 shows the composition, determined by gas chromatography, of the reaction mixtures after a reaction time of 3 hours.

TABLE 3

| Example | T (°C.) | CP | BCP | HB | Remainder | BCP/HB |
|---|---|---|---|---|---|---|
| 13 | 150 | 16.4 | 64.3 | 16.0 | 3.3 | 4.0 |
| 14 | 175 | 19.4 | 60.9 | 16.1 | 3.6 | 3.8 |
| 15 | 200 | 17.7 | 63.1 | 15.3 | 3.9 | 4.1 |

Table 3 shows that the reaction proceeds adequately quickly even at 150° C. In the temperature range selected, only a slight change in the BCP:HB ratio is observed at different temperatures and with similar conversion.

EXAMPLES 16-17

6.5 g of CP and benzylating agent in the molar ratio specified were kept at 200° C. for 3 hours with 3.0 g of Na-Y zeolite. Table 4 shows the composition, determined by gas chromatography, of the reaction mixture.

TABLE 4

| Example | Benzylating agent | C/P benz. a. | CP | BCP | HB | Remainder |
|---|---|---|---|---|---|---|
| 16 | DEB | 2 | 13.0 | 66.2 | 18.0 | 2.8 |
| 17 | CPBE | 1 | 26.1 | 57.7 | 14.5 | 1.7 |

DPBE and CPBE were removed as byproducts in the initial fraction of distillative purification of the reaction mixture. As Table 4 shows, these byproducts can be converted into BCP by addition of CP.

EXAMPLES 18 AND 19

PC and BA were mixed in the molar ratio 4:1 and heated at 200° C. for several hours with a faujasite-type zeolite (20 g/mol of PC). Table 5 shows the reaction time and the composition, determined by gas chromatography, of the reaction mixtures.

TABLE 5

| Example | Zeolite | t/h | PC | BPC | HB | Remainder | BPC/HB |
|---|---|---|---|---|---|---|---|
| 18 | Na—Y | 15 | 35.5 | 59.9 | 3.9 | 0.7 | 15.4 |
| 19 | Sn—Y | 5.5 | 38.5 | 56.1 | 4.0 | 1.4 | 14.0 |

Table 5 shows that the use of faujasite-type zeolites leads to good conversions and excellent selectivities even on benzylation of PC. The yield, relative to reacted PC, is 94%.

What is claimed is:

1. A process for the preparation of p-substituted o-benzylphenol comprising reacting a p-substituted phenol with a benzylating agent selected from the group consisting of benzyl alcohol, benzyl chloride, dibenzyl ether and p-chlorophenyl benzyl ether in the presence of a condensing agent at a temperature of 100° to 250° C., wherein the condensing agent is a zeolite of the faujasite type.

2. The process of claim 1 wherein the faujasite type zeolite is a synthetic zeolite.

3. The process of claim 2 wherein the synthetic zeolite is a zeolite X, a zeolite Y or a mixture of zeolite X and zeolite Y.

4. The process of claim 1 wherein the faujasite type zeolite is employed in an amount of 1 to 50% by weight, relative to the weight of the phenol employed.

5. The process of claim 1 wherein the faujasite type zeolite is employed in an amount of 5 to 40% by weight, relative to the weight of the phenol employed.

6. The process of claim 1, wherein the p-substituted o-benzylphenol corresponds to the formula

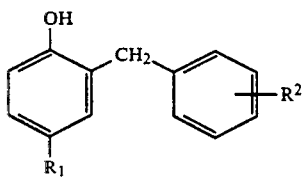 (I)

in which

R$^1$ is halogen, C$_1$-C$_{12}$-alkyl, C$_1$-C$_{12}$-alkoxy or C$_1$-C$_{12}$-alkylmercapto, and R$^2$ is hydrogen, halogen, the cyano group, C$_1$-C$_4$-alkyl or a carb-C$_1$-C$_4$-alkoxy group, the starting p-substituted phenol corresponds to the formula

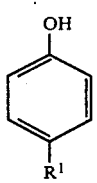 (II)

in which R$^1$ has the meaning given under formula (I), and the benzylating agent corresponds to the formula

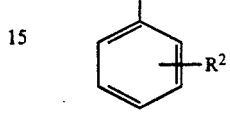 (III)

in which R$^2$ has the meaning given under formula (I) and R$^3$ is halogen, the hydroxyl group, C$_1$-C$_4$-alkoxy, aralkoxy or aryloxy.

7. A process according to claim 1, wherein the temperature is 125° to 220° C.

8. A process according to claim 1, wherein the temperature is 150° to 200° C.

9. A process according to claim 1, wherein the benzylating agent is selected from the group consisting of benzyl alcohol, p-chlorophenyl benzyl ether and dibenzylether.

10. A process according to claim 1, wherein the benzylating agent is benzyl alcohol.

* * * * *